US010351918B2

(12) United States Patent
Lloyd, Jr.

(10) Patent No.: US 10,351,918 B2
(45) Date of Patent: Jul. 16, 2019

(54) PATHOGENESIS QUANTIFICATION SYSTEMS AND TREATMENT METHODS FOR CITRUS GREENING BLIGHT

(71) Applicant: Green Life Biotech, LLC, Ft. Pierce, FL (US)

(72) Inventor: Robert M. Lloyd, Jr., Jensen Beach, FL (US)

(73) Assignee: GREEN LIFE BIOTECH, LLC, Fort Pierce, FL (US)

( * ) Notice: Subject to any disclaimer, the term of this patent is extended or adjusted under 35 U.S.C. 154(b) by 307 days.

(21) Appl. No.: 15/142,576

(22) PCT Filed: Oct. 30, 2014

(86) PCT No.: PCT/US2014/063181
§ 371 (c)(1),
(2) Date: Apr. 29, 2016

(87) PCT Pub. No.: WO2015/066341
PCT Pub. Date: May 7, 2015

(65) Prior Publication Data
US 2016/0319379 A1 Nov. 3, 2016

Related U.S. Application Data

(60) Provisional application No. 61/897,626, filed on Oct. 30, 2013.

(51) Int. Cl.
C12P 19/34 (2006.01)
C12Q 1/70 (2006.01)
C12Q 1/6888 (2018.01)
C12N 15/82 (2006.01)
C12Q 1/689 (2018.01)

(52) U.S. Cl.
CPC ........... C12Q 1/70 (2013.01); C12N 15/8218 (2013.01); C12Q 1/689 (2013.01); C12Q 1/6888 (2013.01); C12Q 2600/136 (2013.01); C12Q 2600/16 (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,469,863 A | 9/1984 | Ts'o et al. | |
| 4,683,195 A | 7/1987 | Mullis et al. | |
| 4,683,202 A | 7/1987 | Mullis | |
| 5,034,506 A | 7/1991 | Summerton et al. | |
| 5,216,141 A | 6/1993 | Benner | |
| 5,235,033 A | 8/1993 | Summerton et al. | |
| 5,386,023 A | 1/1995 | Sanghvi et al. | |
| 5,437,977 A | 8/1995 | Segev | |
| 5,484,908 A | 1/1996 | Froehler et al. | |
| 5,545,527 A | 8/1996 | Stevens et al. | |
| 5,602,240 A | 2/1997 | De Mesmaeker et al. | |
| 5,637,684 A | 6/1997 | Cook et al. | |
| 5,644,048 A | 7/1997 | Yau | |
| 5,645,985 A | 7/1997 | Froehler et al. | |
| 5,795,722 A | 8/1998 | Lacroix et al. | |
| 5,830,653 A | 11/1998 | Froehler et al. | |
| 5,834,189 A | 11/1998 | Stevens et al. | |
| 5,972,716 A | 10/1999 | Ragusa et al. | |
| 5,990,093 A | 11/1999 | Schinazi et al. | |
| 5,990,303 A | 11/1999 | Seela | |
| 6,001,611 A | 12/1999 | Will | |
| 6,007,983 A | 12/1999 | Dunn et al. | |
| 6,033,853 A | 3/2000 | Delair et al. | |
| 6,180,777 B1 | 1/2001 | Horn | |
| 6,265,152 B1 | 7/2001 | Dunn et al. | |
| 6,303,315 B1 | 10/2001 | Skouv | |
| 6,465,175 B2 | 10/2002 | Horn et al. | |
| 6,639,059 B1 | 10/2003 | Kochkine et al. | |
| 6,653,107 B2 | 11/2003 | Dunn et al. | |
| 6,746,864 B1 | 6/2004 | McNeil et al. | |
| 6,800,452 B1 | 10/2004 | McNeil et al. | |
| 6,830,887 B2 | 12/2004 | Lacroix | |
| 6,949,521 B2 | 9/2005 | Chu et al. | |
| 6,974,670 B2 | 12/2005 | Notomi et al. | |
| 7,115,584 B2 | 10/2006 | Schinazi et al. | |
| 7,238,321 B2 | 7/2007 | Wittwer et al. | |
| 7,282,328 B2 | 10/2007 | Kong et al. | |
| 7,402,588 B2 | 7/2008 | Liotta et al. | |
| 7,427,380 B2 | 9/2008 | McNeil et al. | |
| 7,485,428 B2 | 2/2009 | Armes et al. | |
| 7,635,690 B2 | 12/2009 | Schinazi et al. | |
| 7,662,594 B2 | 2/2010 | Kong et al. | |
| 7,666,598 B2 | 2/2010 | Piepenburg et al. | |
| 7,745,135 B2 | 6/2010 | Mori et al. | |
| 7,759,061 B2 | 7/2010 | Piepenburg et al. | |
| 7,763,427 B2 | 7/2010 | Piepenburg et al. | |
| 7,829,284 B2 | 11/2010 | Kong et al. | |
| 7,851,186 B2 | 12/2010 | Nagamine | |
| 8,058,054 B2 | 11/2011 | Owen et al. | |
| 8,168,583 B2 | 5/2012 | Schinazi et al. | |
| 8,415,321 B2 | 4/2013 | Schinazi et al. | |
| 9,758,837 B2* | 9/2017 | Duan | C12Q 1/689 |
| 10,023,920 B2* | 7/2018 | Duan | C12Q 1/689 |
| 2003/0092905 A1 | 5/2003 | Kochkine et al. | |
| 2004/0214800 A1 | 10/2004 | Levy et al. | |

OTHER PUBLICATIONS

PCT International Search Report and Written Opinion for PCT Application No. PCT/US2014/063181 dated Feb. 19, 2015 (10 pages).

(Continued)

Primary Examiner — Kenneth R Horlick
(74) Attorney, Agent, or Firm — Allen, Dyer, Doppelt + Gilchrist, P.A.

(57) ABSTRACT

The invention relates to a novel pathogenesis model, method, or kit for detecting pathogenesis in a subject. In particular, the invention provides a pathogen index derived from a ratio of the amount of dual pathogen targets relative to the amount of host quantitative measures. The pathogen index is used in diagnosis, prognosis, and/or treatment strategy of any disease, including citrus greening diseases (HLB). Research tools and methods for screening drugs for treating or preventing citrus greening diseases, as well as treatment or prevention methods for citrus greening diseases are also provided.

10 Claims, 5 Drawing Sheets

(56) References Cited

OTHER PUBLICATIONS

Li et al., "Quantitative Real-Time PCR for Detection and Identification of *Candidatus liberibacter* Species Associated with Citrus Huanglongbing," Journal of Microbiological Methods, 2006, 66(1)104-115.

Zhang et al., "Chemical Compunds Effective Against the Citrus Huanglongbing Bacterium 'Candidatus Liberibacter Asiaticus' in Planta," Bacteriology, 2011, 101(9):1097-1103.

Zhang et al., "Screening Molecules for Control of Citrus Huanglongbing Using an Optimized Regeneration System fo 'Candidatus Liberibacter Asiaticus'-Infected Periwinkle (*Catharanthus roseus*) Cuttings," Bacteriology, 2010, 100 3):239-245.

Zhang et aL, "'Ca. Liberibacter Asiaticus' Carries an Excision Plasmid Prophage and a Chromosomally Integrated Prophage that Becomes Lytic in Plant Infections," Molecular Plant-Microbe Interactions, 2011, 24(4):458-468.

Bennett et al., "Utility of the Bacteriophage RB69 Polymerase gp43 as a Surrogate Enzyme for Herpesvirus Orthologs," Viruses, 2013, 5:54-86.

Citrus Advanced Technology Program, Quarterly & Final Reports: Control of Citrus Greening, Canker & Emerging Diseases of Citrus, Jun. 2013.

Deghorain et al., "The Staphylococci Phages Family: An Overview," Viruses, 2012, 4:3316-3335.

Duerkop et al., "A Composite Bacteriophage Alters Colonization by an Intestinal Commensal Bacterium," PNAS, 2012, 109(43):17621-17626.

Elwell et al., "Antibacterial Activity and Mechanism of Action of 3'-Azido-3'-Deoxythymidine (BW A509U)," Antimicrobial Agents and Chemotherapy, 1987, 274-280.

Ishihama et al., "2'-Deoxy-2'-Azidoadenosine Triphosphate and 2'-Deoxy-2'-Fluoroadenosine Triphosphate as Substrates and Inhibitors for *Escherichia coli* DNA-Dependent RNA Polymerase," J. Biochem, 1980, 87:825-830.

Nageswara-Rao et al., "Development of Rapid, Sensitive and Non-Radioactive Tissue-Blot Diagnostic Method for the Detection of Citrus Greening," Molecular and Cellular Probes, 2013, pp. 1-8.

Sechler et al., "Cultivation of 'Candidatus Liberibacter Asiaticus', 'Ca. L. Africanus', and 'Ca. L. americanus' Associated with Huanglongbing," Phytopathology, 2009, 99(5):480-486.

Saponari et al., "Validation of high-throughput real time polymerase chain reaction assays for simultaneous detection of invasive citrus pathogens," Journal of Virological Methods, 2013, 193(2):478-486.

Tatineni et al., "In Planta Distribution of 'Candidatus Liberibacter Asiaticus' as Revealed by Polymerase Chain Reaction (PCR) and Real-Time PCR," Phytopathology, 2008, 98(5):592-599.

Villechanoux et al., "The Genome of the Non-Cultured, Bacterial-Like Organism Associated with Citrus Greening Disease Contains the nusG-rplKAJL-rpoBC Gene Cluster and the Gene for a Bacteriophage Type DNA Polymerase," Curr Microbiol.; Mar. 1993; 26(3):161-6; Abstract only; 1 page.

Leonard et al., "Complete Genome Sequence of Liberibacter Crescens BT-1," Stand Genomic Sci.; Dec. 19, 2012; 7(2):271-83; Abstract only; 1 page.

Cao et al., "Clinical Evaluation of Branched DNA Signal Amplification for Quantifying HIV Type 1 in Human Plasma," AIDS Res Hum Retroviruses; Mar. 1995; 11(3):353-61; Abstract only; 1 page.

Wells et al., "Cleavage and Analysis of Material from Single Resin Beads," Journal of Organic Chemistry; American Chemical Society; 1998; 63(19), 6430-6431; pp. 1-18.

Altschul et al., "Basic Local Alignment Search Tool," J Mol Biol.; Oct. 5, 1990; 215(3):403-10; Abstract only; 1 page.

Gish et al., "Identification of Protein Coding Regions by Database Similarity Search," Nat Genet.; Mar. 1993; 3(3):255-72; Abstract only; 1 page.

Madden et al., "Applications of Network BLAST Server," Methods Enzymol.; 1996; 266:131-41; Abstract only; 1 page.

Altschul et al., "Gapped BLAST and PSI-BLAST: A New Generation of Protein Database Search Programs," Nucleic Acids Res., Sep. 1, 1997; 25(17):3389-402; Abstract only; 1 page.

Zhang et al., "PowerBLAST: A New Network BLAST Application for Interactive or Automated Sequence Analysis and Annotation," Genome Research; Aug. 27, 2017; 7:649-656.

Lyttle et al., "A New Universal Linker for Solid Phase DNA Synthesis," Nucleic Acids Res.; Jul. 15, 1996; 24(14):2793-8; Abstract only; 1 page.

Shchepinov et al., "Design of Multidye Systems for FRET-Based Applications," Nucleosides Nucleotides Nucleic Acids; Apr.-Jul. 2001; 20(4-7):369-74; Abstract only; 1 page.

Doronina et al., "Efficient Synthesis of Oligonucleotide-Peptide Conjugates on Large Scale," Nucleosides Nucleotides Nucleic Acids; Apr.-Jul. 2001; 20(4-7):1007-10; Abstract only; 1 page.

Trawick et al., "Enhancing Sequence-Specific Cleavage of RNA Within a Duplex Region: Incorporation of 1,3-propanediol Linkers into Oligonucleotide Conjugates of Serinol-Terpyridine," Bioconjug Chem.; Nov.-Dec. 2001; 12(6):900-5; Abstract only; 1 page.

Olejnik et al., "Photocleavable Affinity Tags for Isolation and Detection of Biomolecules," Methods in Enzymology; vol. 291; 1998; pp. 135-154; Abstract only; 2 pages.

Pljevaljcic et al., "Design of a New Fluorescent Cofactor for DNA Methyltransferases and Sequence-Specific Labeling of DNA," J Am Chem Soc.; Mar. 26, 2003; 125(12):3486-92; Abstract only; 1 page.

Sprinz et al., "Enzymatic Incorporation of ATP and CTP Analogues into the 3'end of tRNA," Eur J Biochem.; Dec. 1977; 81(3):579-89; Abstract only; 1 page.

Letsinger et al., "Effects of Pendant Groups at Phosphorus on Binding Properties of d-ApA Analogues," Nucleic Acids Res.; Apr. 25, 1986; 14(8):3487-99; Abstract only; 1 page.

Sawai, "Synthesis and Properties of Oligoadenylic Acids Containing 2'-5' Phosphoramide Linkage," Chemistry Letters; The Chemical Society of Japan; Mar. 7, 1984; pp. 805-808.

Letsinger et al., "Cationic Oligonucleotides," Journal of the American Chemical Society; Jun. 1988; 110(13); pp. 4470-4471; First Page of Article Only; 2 pages.

Mag et al., "Synthesis and Selective Cleavage of an Oligodeoxynucleotide Containing a Bridged Internucleotide 5'-Phosphorothioate Linkage," Nucleic Acids Res.; Apr. 11, 1991; 19(7):1437-41; Abstract only; 1 page.

Egholm et al., "Peptide Nucleic Acids (PNA), Oligonucleotide Analogs with an Achiral Peptide Backbone," Journal the American Chemical Society; Feb. 1992; 114(5); pp. 1895-1897; First Page of Article Only; 2 pages.

Meier et al., "Peptide Nucleic Acids (PNAs)—Unusual Properties of Nonionic Oligonucleotide Analogues," Angewandte Chemie International Edition in English; vol. 31; Issue 8; Aug. 1992; Abstract only; 1 page.

Egholm et al., "PNA Hybridizes to Complementary Oligonucleotides Obeying the Watson-Crick Hydrogen-Bonding Rules," Nature; Oct. 7, 1993; 365(6446):566-8; Abstract only; 1 page.

Dempcy et al., "Synthesis of a Thymidyl Pentamer of Deoxyribonucleic Guanidine and Binding Studies with DNA Homopolynucleotides," Proc Natl Acad Sci USA; Jun. 20, 1995; 92(13):6097-101; Abstract only; 1 page.

Jung et al., "Hybridization of Alternating Cationic/Anionic Oligonucleotides to RNA Segments," Nucleosides and Nucleotides; vol. 13; Issue 6-7; Feb. 7, 1994; pp. 1597-1605; Abstract only; 1 page.

Horn et al., "Oligonucleotides with Alternating Anionic and Cationic Phosphoramidate Linkages: Synthesis and Hybridization of Stereo-Uniform Isomers," Tetrahedron Letters; vol. 37; Issue 6; Feb. 5, 1996; pp. 743-746; Abstract only; 1 page.

Seela et al., "3-Deazaguanine N7- and N9-(2'-Deoxy-β-D-ribofuranosides): Building Blocks for Solid-Phase Synthesis and Incorporation into Oligodeoxyribonucleotides," Helvetica Chimica Acta; vol. 74; Issue 8; Dec. 11, 1991; Abstract only; 1 page.

Grein et al., "3-Deaza- and 7-Deazapurines: Duplex Stability of Oligonucleotides Containing Modified Adenine or Guanine Bases," Bioorganic & Medicinal Chemistry Letters; vol. 4; Issue 8; Apr. 21, 1994; pp. 971-976; Abstract only; 2 pages.

(56) References Cited

OTHER PUBLICATIONS

Seela et al., "Oligonucleotides Containing Pyrazolo[3,4-d]pyrimidines: The Influence of 7-Substituted 8-Aza-7-deaza-2'-deoxyguanosines on the Duplex Structure and Stability," Helvetica Chimica Acta; vol. 82; Issue 10; Oct. 11, 1999; Abstract only; 1 page.
Narang et al., "Improved Phosphotriester Method for the Synthesis of Gene Fragments," Methods in Enzymology; vol. 68; 1979; pp. 90-98; Abstract only; 1 page.
Brown et al., "Chemical Synthesis and Cloning of a Tyrosine tRNA Gene," Methods in Enzymology; vol. 68; 1979; pp. 109-151; Abstract only; 1 page.
Beaucage et al., "Deoxynucleoside Phosphoramidites—A New Class of Key Intermediates for Deoxypolynucleotide Synthesis," Tetrahedron Letters; vol. 22; Issue 20; 1981; pp. 1859-1862; Abstract only; 1 page.
Matteucci et al., "Synthesis of Deoxyoligonucleotides on a Polymer Support," Journal of the American Chemical Society; Jun. 1981; 103(11); pp. 3185-3191; First Page of Article Only; 2 pages.

\* cited by examiner

PATHOGENESIS QUANTIFICATION SYSTEMS AND TREATMENT METHODS FOR CITRUS GREENING BLIGHT

CROSS-REFERENCE TO RELATED APPLICATIONS

This application claims priority to PCT Application No. PCT/US2014/063181 filed Oct. 30, 2014, which claims priority to U.S. Provisional Application Ser. No. 61/897,626, filed Oct. 30, 2013, entitled "Pathogenesis Quantification Systems and Treatment Methods for Citrus Greening Blight", the entire contents of which are incorporated by reference herein.

FIELD OF THE INVENTION

The present invention relates particularly to detection and control of phage and bacteria that are pathogenic to host plants and mammals.

The present invention is exemplified in the context of the citrus greening blight, also known as Huanglongbing (HLB), and more generally relates to testing and treatment methods and compositions based on determination of a pathogenic index from a dual pathogen: multiplex host quantification ratio or quartile of pathogenesis designed specifically for diagnosis and treatment of quartiles and secondarily for drug development, and as a research tool for the identification of drugs candidates.

BACKGROUND OF THE INVENTION

Citrus greening blight, also known as Huanglongbing (HLB), is a lethal disease in citrus plants across the world, causing significant fruit loss and death of infected trees. HLB infection affects the leaves, twigs and fruit of the tree, eventually causing the whole tree to decline. Symptoms of HLB include blotchy, mottled and yellow-veined leaves, lopsided and small, green, salty and bitter flavored fruit, twig dieback, and overall tree stunting and decline. Diagnosis of HLB is complicated by the fact that some of the symptoms of HLB are similar to symptoms of other tree ailments, including nutritional deficiency. HLB control often requires destroying infected trees, which may not even show symptoms of HLB for several years after becoming infected.

Polymerase chain reaction diagnostic testing has identified the major pathogen associated with symptoms of HLB as the bacterium *Candidatus Liberibacter* spp, including the *Ca. L. asiaticus* (LAS), *Ca. L. africanus* and *Ca. L. americanus* species. The bacteria is believed to impair nutrient transfer in a citrus tree's phloem and leaf stems, wherein the plant pathology is suspected to be caused by nutrient deficiency. Antibiotic control of the putative causative bacterium is a passive solution but an expensive means of grove management that couldnever be a plausible solution. Low replication levels of *Ca. L.* in citrus require high sensitivity methods to detect their presence. PCR based methods that have been employed for the detection of *Ca. L. asiaticus* bacterium include qualitative PCR assays (Saponari et al., 2013, J. Virol. Methods. 193(2): 478-86) and tissue-blot diagnosis (Nageswara-Rao M. et al., 2013, Mol. Cell Probes. 27(5-6): 176-83), each of which are herein incorporated by reference.

Bacteriophages or phages are viruses which infect bacteria. The majority are DNA viruses. Each phage attacks only particular species or in many cases only certain strain within the species. Structurally, a bacteriophage or phage is composed of a polygonal head consisting of DNA surrounded by a thin protein membrane and a short straight tail consisting of protein. However, spherical and filamentous phages have also been reported. The life cycle of bacteriophages includes two cycles: vegetative cycle and lysogenic cycle. In the vegetative cycle, the phage is called virulent phage, and the cycle contains the steps of attachment (adsorption), penetration, eclipse phase, replication, assembly, and release. In the lysogenic cycle, the phage is called temperate phage, and the cycle contains the steps of attachment (adsorption), penetration, eclipse phase, and then unlike the virulent phage in the vegetative cycle, the temperate phage after the eclipse phase does not replicate, instead, it is integrated into the bacterial chromosome and remains latent for a period of time. The integrated phage is now called prophage, and the bacteria carrying prophage is called lysogen. The lysogen is not lysed but grows and multiplies with prophage as a part of the chromosome. The lysogen can acquire new properties, and the prophage may revert to virulent phage and infected bacteria may be lysed. The practical applications of bacteriophages include, but are not limited to, bacteriophage typing, classification of bacteria into phage groups, phage lysogenic conversion, phage therapy, and as cloning vectors.

Bacteriophages such as those associated with *Staphylococci* and the intestinal commensal bacterium *E. faecalis* are deemed important factors in the life cycle of host bacteria that may affect the pathogenicity of the host (Deghorain and Melderen, 2012, Viruses 4:3316-35; Duerkop et al., PNAS 109(43):17621-626). Analysis of the *Ca. L. asiaticus* genome derived from HLB symptomatic citrus has revealed the presence of two circular phage genomes, SC1 and SC2 (Zhang et al., 2011, Molecular Plant-Microbe Interactions 24(4):458-68). Three DNA fragments (In-2.6, In-1.0 and In-0.6) of the non-cultured, bacterial-like organism (BLO) associated with citrus greening disease were cloned, and nucleotide sequence determination showed that the genome of the non-cultured BLO associated with citrus greening disease contains the nusG-rp1KAJL-rpoBC gene cluster and the gene for a bacteriophage type DNA polymerase (Villechanoux et al., 1993, Curr Microbiol. 26(3):161-6), the entire contents of this reference is incorporated by reference herein. Complete genome of *Liberibacter crescens* BT-1 was sequenced and contains more genes in thiamine and essential amino acid biosynthesis, as well as contains two prophage regions (Leonard et al., 2012, Standards in Genomic Sciences 7:271-83), the entire contents of which is incorporated by reference herein.

In light of the foregoing, there still remains a need in the art for HLB diagnosis methods and eradication methods and compositions for the disease, as well as more generally diagnostic and treatment methods and compositions for pathogen-pathogenic-host mediated disease systems.

SUMMARY OF THE INVENTION

Various embodiments described herein provide a novel pathogenesis model for diagnostic, prognostic, drug screening, and treatment methods and related algorithms useful for detecting pathogenesis in a biological sample. In certain embodiments, the invention provides a method for detecting pathogenesis in a biological sample, comprising: a) quantifying the amount of a nucleic acid in the sample specific for a first organism that is a pathogen associated with a second organism that in tandem these two organisms affects a host organism to determine a pathogen quantitative measurement, b) quantifying the amount of a nucleic acid in the sample specific for the host organism response to pathogens to determine a multiplex quantitation for targets associated with the pathogenesis of the disease; and c) calculating the ratio of the amount of dual pathogen targets relative to the amount of host quantitative measures, wherein said ratio provides a pathogen index for detecting pathogenesis. In certain embodiments, a greater pathogen index indicates a poorer prognosis and can be used for drug treatment efficacy and drug screening.

In certain embodiments, the quantification of the nucleic acid in the sample specific for the first organism is performed by contacting the nucleic acid from the sample with a first set of oligonucleotide primers in a nucleic acid amplification reaction, the first set of oligonucleotides being at least partially complementary to the nucleic acid of the first organism, and wherein the quantification of the nucleic acid in the sample specific for the second organism is performed by contacting the nucleic acid from the sample with a second set of oligonucleotide primers in a nucleic acid amplification reaction, the second set of oligonucleotides being at least partially complementary to the nucleic acid of the second organism, and further comprising detecting amplicons from the nucleic acid amplification reactions, and wherein the quantification of the nucleic acid in the sample specific for the third host organism is performed by contacting the nucleic acid from the sample with a third set of oligonucleotide primers in a nucleic acid amplification reaction, the third set of oligonucleotides being at least partially complementary to the nucleic acid of the third organism, and further comprising detecting amplicons from the nucleic acid amplification reactions wherein the amplification reactions occur in the same container, and calculating the ratio of the amount of pathogen ratio relative to the amount of host load based on the relative number of amplicons to derive the pathogen index or quartile. As used herein, the pathogen organism is a virus and bacteria, and the host organism is plant or animal. When the host organism is a bacteria, the host may also reside within or in association with another host, such as a plant or animal, e.g., human. In certain embodiments, the pathogenesis is citrus green blighting or Huanglongbin (HLB), the pathogen or the first organism can be a bacterio-phage or virus, and the second organism is *Candidatus Liberibacter asiaticus* (LAS) bacteria and the host is a wide array of fruiting and non-fruiting plants. The pathogen index may also be derived from a further correlation with any inducer or factor gene pathogenically tied together with the dual pathogen to host relationship.

In certain embodiments, the inventive method further comprises a report algorithm correlated with the pathogen index or quartile providing clinical utility as a treatment strategy. In some embodiments, the inventive method further comprises a step of quantifying the amount of a nucleic acid in the sample specific for an inducer of the pathogen organism to determine an inducer load; and wherein the pathogen index and the inducer load are correlated with the report index for determining prognosis and providing clinical utility as a treatment strategy. The inventive method further provides that multiple unique nucleic acids specific to the pathogen organisms, the host organism or the inducer are quantified and correlated in the report index.

The nucleic acid quantified in the invention includes, but is not limited to, RNA or DNA. In certain embodiments, the phage RNA and the bacterial DNA are quantified, and a ratio of phage RNA to bacterial DNA is calculated to derive a pathogen index. The nucleic acid can be amplified for relative quantitative determination by any conventional nucleic acid detection reaction now known or later developed including, but not limited to standard polymerase chain reaction (SPCR), real-time PCR, recombinase polymerase amplification (RPA), helicase-dependent amplification (HAD), loop mediate isothermal amplification (LAMP), and nicking enzyme amplification reaction (NEAR).

In certain embodiments, the invention provides a kit for detecting a pathogenesis, such as citrus greening blight (HLB), in a sample, comprising: a) at least a first set of oligonucleotides being at least partially complementary to a nucleic acid of a first pathogen organism in the sample that is pathogenically associated with a second organism that in tandem these two pathogens affects a host organism to determine a pathogen quantitative measurement, b) at least a second set of oligonucleotides being at least partially complementary to a nucleic acid of the host organism response to the pathogen of the disease, c) reagents for nucleic acid amplification reactions with the first and second sets of oligonucleotides; d) instructions for conducting the nucleic acid amplification reactions and detecting one or more amplicons thereof; and e) instructions for calculating a ratio of the amplicons and/or the amount of dual pathogen targets relative to the amount of host quantitative measures, wherein said ratio provides a pathogen index for detecting, prognosis, drug screening, and treatment strategy or efficacy for the pathogeneis, such as citrus greening blight (HLB).

The invention further provides a method for screening a candidate therapeutic agent for inhibition or prevention of citrus greening blight. The invention method comprises the steps of providing a culture of *Candidatus Liberibacter* with a bacteriophage having a repressed phage lytic cycle; combining the culture with a candidate therapeutic agent candidate; and detecting inhibition of growth of the *Candidatus Liberibacter* culture indicating that the candidate therapeutic agent inhibits or prevents citrus greening blight. In certain embodiments, the bacteriophage is a lytic phage, including but not limited to, SC1, SC2, and SC3 lytic phage, and wherein the phage lytic cycle is repressed or genetically deleted.

The invention also provides a method for treating and/or preventing bacteriophage or viral infection in bacteria, plant or animal individual, said method comprising administering to the individual in need a composition comprising an effective amount of an agent selected from the group consisting of nucleoside, non-nucleoside, nucleotide, non-nucleotide, ribonucleoside, and a ribonucleoside analog that selectively inhibits viral replication. In certain embodiments, the bacteriophage infection is in a *Candidatus Liberibacter* in a citrus tree that results in citrus greening blight, such as HLB or LAS. In certain embodiments, an antiviral agent is used to treat and/or prevent HLB or LAS. The invention contemplates different classes of antiviral agents, now known or later developed, including but not limited to, natural antiviral compounds, such as interferon-α (IFN-α) with maximal antiviral activity and interferon-β (IFN-β) with intermediate activity, and synthetic antiviral agents, which based on their point of action in the viral replication cycle, are divided into the following groups: 1) nucleoside analogs, such as acyclovir (ACV) and its pro-drug valacyclovir, ribavirin, zidovudin, and azidothymidine (AZT), which block viral nucleic acid synthesis; 2) nucleotide analogs, e.g., cidofovir (CDV), ganciclovir (GCV) (or valganciclovir) which differ from nucleoside analogs by having an attached phosphate group. The nucleotide analogs can persist in cells for long periods of time; 3) non-nucleoside reverse transcriptase inhibitor, e.g., nevirapine, which bind to reverse transcriptase; 4) protease inhibitors, e.g., saquinavir, which inhibits viral protease; and 5) other types, such as amantidine and rimantidine which inhibit influenza viruses by inhibiting viral uncoating, and/or the pyrophosphate analog phosphonoformic (PFA, foscarnet) which inhibits reverse transcriptase in HIV and viral polymerase in Herpes viruses (see e.g., Bennett and Gotte, 2013, Viruses 5:54-86, the review aims to discuss strengths, limitations, and opportunities of the phage surrogate with emphasis placed on its utility in the discovery and development of antiherpetic drugs), the entire contents of which is incorporated by reference herein.

In certain embodiments, the antiviral agents are ATP analogs, such as 2'-deoxy-2'-azidoadenosine 5'-triphosphate (AzTP) and/or 2'-deoxy-2'-fluoroadenosine 5'-triphophate (AfTP), which inhibits RNA synthesis by *E. coli* RNA polymerase (Ishihama et al., 1980, J. Biochem. 87: 825-30), the entire content of which is incorporated by reference herein. In other embodiments, the antiviral agents are azidothymidine (AZT), the thymidine analog 3'-azido-3'-deoxythymidine (aka BW A509U), which has potent bacterial activity against many members of the family Enterobacteriaceae, and the AZT-triphosphate is the most potent inhibitor of replicative DNA synthesis, and/or a specific DNA chain terminator in the in vitro DNA polymerization reaction, which may explain the lethal properties of this compound against susceptible microorganisms (Elwell et al., 1987, Antimicrobial Agents and Chemotherapy, 31(2): 274-80), the entire contents of which is incorporated by reference herein.

In certain embodiments, the treatment method can further comprise a nucleotide pool reducer, such as hydroxyurea in an effective amount. In some embodiments, the treatment composition further comprises a surfactant or penetrant for enhancing delivery of the composition to a targeted location (such as a leaf) of the affected plant.

DETAILED DESCRIPTION OF THE INVENTION

Figure 1:
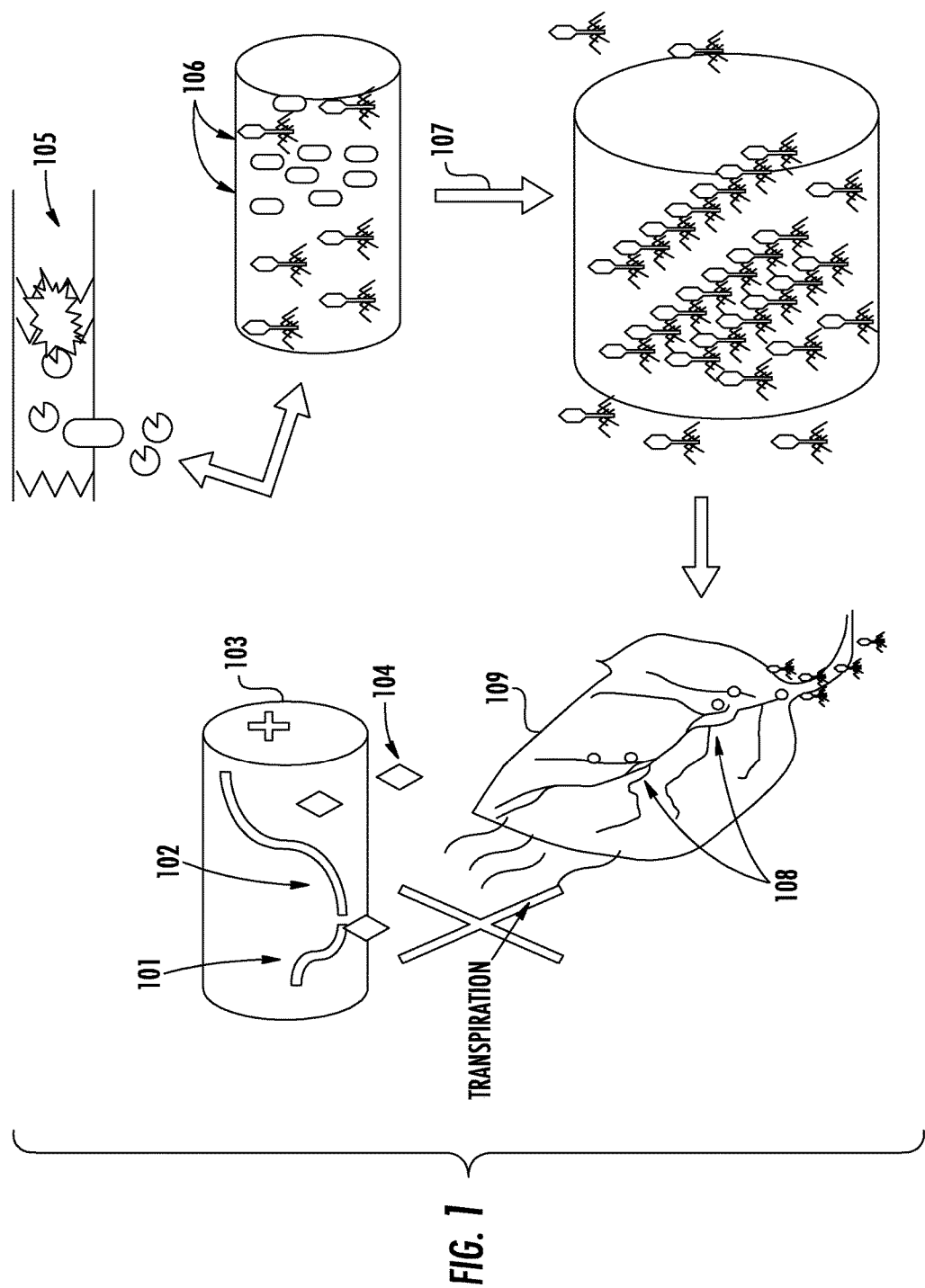
FIG. 1 illustrates a novel pathogenesis model.

It is to be understood that the invention is not limited in its application to the details of and the arrangement of components set forth in the following description. It is also to be understood that this invention is not limited to particular oligonucleotide probes, methods, compositions, reaction mixtures, kits, systems, computers, or computer readable media, which can, of course, vary. It is further to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. Each of the references cited herein is incorporated by reference in its entirety. In describing and claiming the present invention, the following terminology and grammatical variants will be used in accordance with the definitions set forth below.

Definitions:

An "amplification reaction" refers to a primer initiated replication of one or more target nucleic acid sequences or complements thereto.

An "amplicon" refers to a molecule made by copying or transcribing another molecule, e.g., as occurs in transcription, cloning, and/or in a technique such as polymerase chain reaction ("PCR") (e.g., strand displacement PCR amplification (SDA), duplex PCR amplification, real-time PCR, recombinase polymerase amplification (RPA), helicase-dependent amplification (HAD), loop mediate isothermal amplification (LAMP), and nicking enzyme amplification reaction (NEAR)) or other nucleic acid amplification technique. Typically, an amplicon is a copy of a selected nucleic acid (e.g., a template or target nucleic acid) or is complementary thereto.

An "amplified signal" refers to increased detectable signal that can be produced in the absence of, or in conjunction with, an amplification reaction. Exemplary signal amplification techniques are described in, e.g., Cao et al. (1995) "Clinical evaluation of branched DNA signal amplification for quantifying HIV type 1 in human plasma," AIDS Res Hum Retroviruses 11(3):353-361, and in U.S. Pat. No. 5,437,977 to Segev, U.S. Pat. No. 6,033,853 to Delair et al., and U.S. Pat. No. 6,180,777 to Horn, which are each incorporated by reference.

The term "attached" or "conjugated" refers to interactions and/or states in which material or compounds are connected or otherwise joined with one another. These interactions and/or states are typically produced by, e.g., covalent bonding, ionic bonding, chemisorption, physisorption, and combinations thereof. In certain embodiments, for example, oligonucleotide probes are attached to solid supports. In some of these embodiments, an oligonucleotide probe is conjugated with biotin (i.e., is biotinylated) and a solid support is conjugated with avidin such that the probe attaches to the solid support via the binding interaction of, e.g., biotin and avidin.

Molecular species "bind" when they associate with one another via covalent and/or non-covalent interactions. For example, two complementary single-stranded nucleic acids can hybridize with one another to form a nucleic acid with at least one double-stranded region. To further illustrate, antibodies and corresponding antigens can also non-covalently associate with one another.

The term "cleavage" refers to a process of releasing a material or compound from attachment to another material or compound. In certain embodiments, for example, oligonucleotides are cleaved from, e.g., a solid support to permit analysis of the oligonucleotides by solution-phase methods. See, e.g., Wells et al. (1998) "Cleavage and Analysis of Material from Single Resin Beads," J. Org. Chem. 63:6430, which is incorporated by reference.

A "character" when used in reference to a character of a character string refers to a subunit of the string. In one embodiment, the character of a character string encodes one subunit of an encoded biological molecule. Thus, for example, where the encoded biological molecule is a polynucleotide or oligonucleotide, a character of the string encodes a single nucleotide.

A "character string" is any entity capable of storing sequence information (e.g., the subunit structure of a biological molecule such as the nucleotide sequence of a nucleic acid, etc.). In one embodiment, the character string can be a simple sequence of characters (letters, numbers, or other symbols) or it can be a numeric or coded representation of such information in tangible or intangible (e.g., electronic, magnetic, etc.) form. The character string need not be "linear," but can also exist in a number of other forms, e.g., a linked list or other non-linear array (e.g., used as a code to generate a linear array of characters), or the like. Character strings are typically those which encode oligonucleotide or polynucleotide strings, directly or indirectly, including any encrypted strings, or images, or arrangements of objects which can be transformed unambiguously to character strings representing sequences of monomers or multimers in polynucleotides, or the like (whether made of natural or artificial monomers).

The term "complement thereof" refers to nucleic acid that is both the same length as, and exactly complementary to, a given nucleic acid.

A "composition" refers to a combination of two or more different components. In certain embodiments, for example, a composition includes a solid support that comprises one or more oligonucleotide probes, e.g., covalently or non-covalently attached to a surface of the support. In other embodiments, a composition includes one or more oligonucleotide probes in solution.

The term "deletion" in the context of a nucleic acid sequence refers to an alteration in which at least one nucleotide is removed from the nucleic acid sequence, e.g., from a 5'-terminus, from a 3'-terminus, and/or from an internal position of the nucleic acid sequence.

The term "derivative" refers to a chemical substance related structurally to another substance, or a chemical substance that can be made from another substance (i.e., the substance it is derived from), e.g., through chemical or enzymatic modification. To illustrate, oligonucleotide probes are optionally conjugated with biotin or a biotin derivative. To further illustrate, one nucleic acid can be "derived" from another through processes, such as chemical synthesis based on knowledge of the sequence of the other nucleic acid, amplification of the other nucleic acid, or the like.

The term "selectively bind" or "selective binding" in the context of nucleic acid detection reagents refers to a nucleic acid detection reagent that binds to one or more target nucleic acid or a substantially identical variant or complement thereof to a greater extent than the nucleic acid detection reagent binds, under the same hybridization conditions, to non-target nucleic acids. The term "detectably bind" refers to binding between at least two molecular species (e.g., a probe nucleic acid and a target nucleic acid, a sequence specific antibody and a target nucleic acid, etc.) that is detectable above a background signal (e.g., noise) using one or more methods of detection. The term "selectively detect" refers to the ability to detect one or more target nucleic acid or a substantially identical variant or complement thereof to a greater extent than non-target nucleic acids from organisms.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extended primer nucleic acid" refers to a primer nucleic acid to which one or more additional nucleotides have been added or otherwise incorporated (e.g., covalently bonded thereto).

Nucleic acids "hybridize" or "bind" when they associate with one another, typically in solution. Nucleic acids hybridize due to a variety of well characterized physio-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, N.Y.), as well as in Ausubel (Ed.) Current Protocols in Molecular Biology, Volumes I, II, and III, 1997, which is incorporated by reference. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides. Both Hames and Higgins 1 and 2 are incorporated by reference.

"Stringent hybridization wash conditions" in the context of nucleic acid hybridization assays or experiments, such as nucleic acid amplification reactions, Southern and northern hybridizations, or the like, are sequence dependent, and are different under different environmental parameters. An extensive guide to the hybridization of nucleic acids is found in Tijssen (1993), supra. and in Hames and Higgins, 1 and 2. For purposes of the present invention, generally, "highly stringent" hybridization and wash conditions are selected to be at least about 5° C. lower than the thermal melting point ($T_m$) for the specific sequence at a defined ionic strength and pH. The $T_m$ is the temperature (under defined ionic strength and pH) at which 50% of the test sequence hybridizes to a perfectly matched probe. Very stringent conditions are selected to be equal to the $T_m$ for a particular probe.

An example of stringent hybridization conditions for hybridization of complementary nucleic acids on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook et al., Molecular Cloning: A Laboratory Manual, 3rd Ed., Cold Spring Harbor Laboratory Press, Cold Spring Harbor, N.Y. (2001), which is incorporated by reference, for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

Comparative hybridization can be used to identify nucleic acids or preferred primers for complementary nucleic acid sets for amplification of the invention. In particular, detection of stringent hybridization in the context of the present invention indicates strong structural similarity to, e.g., the nucleic acids of the desired bacterial, phage, virus, etc. For example, it is desirable to identify test nucleic acids that hybridize to the exemplar nucleic acids herein under stringent conditions. One measure of stringent hybridization is the ability to detectably hybridize to one of the desired nucleic acids (e.g., nucleic acids of bacteria and/or phage associated with HLB or other citrus greening blight, and complements thereof) under stringent conditions. Stringent hybridization and wash conditions can easily be determined empirically for any test nucleic acid.

For example, in determining highly stringent hybridization and wash conditions, the stringency of the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the stringency of the hybridization and wash conditions are gradually increased until a probe consisting of or comprising one or more desired nucleic acid sequences and complementary polynucleotide sequences thereof, binds to a perfectly matched complementary target (e.g., a nucleic acid comprising one or more nucleic acid sequences of bacteria and/or phage associated with HLB or other citrus greening blight, and complementary polynucleotide sequences thereof), with a signal to noise ratio that is at least 5× as high as that observed for hybridization of the probe to a non-target nucleic acid. In this case, non-target nucleic acids are those from organisms other than the desired bacteria, phage, virus, etc. Such non-target nucleic acid sequences can be identified in, e.g., GenBank by one of skill in the art. A test nucleic acid is said to specifically hybridize to a probe nucleic acid when it hybridizes at least one-half as well to the probe as to the perfectly matched complementary target, i.e., with a signal to noise ratio at least one-half as high as hybridization of the probe to the target under conditions in which the perfectly matched probe binds to the perfectly matched complementary target with a signal to noise ratio that is at least about 5×-10× as high as that observed for hybridization to the non-target nucleic acids.

Ultra high-stringency hybridization and wash conditions are those in which the stringency of hybridization and wash conditions are increased until the signal to noise ratio for binding of the probe to the perfectly matched complementary target nucleic acid is at least 10× as high as that observed for hybridization to the non-target nucleic acids. A target nucleic acid which hybridizes to a probe under such conditions, with a signal to noise ratio of at least one-half that of the perfectly matched complementary target nucleic acid is said to bind to the probe under ultra-high stringency conditions.

Similarly, even higher levels of stringency can be determined by gradually increasing the stringency of hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to the non-target nucleic acids can be identified. A target nucleic acid which hybridizes to a probe under such conditions, with a signal to noise ratio of at least one-half that of the perfectly matched complementary target nucleic acid is said to bind to the probe under ultra-ultra-high stringency conditions.

"Selectively hybridizing" or "selective hybridization" occurs when a nucleic acid sequence hybridizes to a specified nucleic acid target sequence to a detectably greater degree than its hybridization to non-target nucleic acid sequences. Selectively hybridizing sequences have at least 50%, or 60%, or 70%, or 80%, or 90% sequence identity or more, e.g., typically 95-100% sequence identity (i.e., complementarity) with each other.

A "sequence" of a nucleic acid refers to the order and identity of nucleotides in the nucleic acid. A sequence is typically read in the 5' to 3' direction. The terms "identical" or percent "identity" in the context of two or more nucleic acid or polypeptide sequences, refer to two or more sequences or subsequences that are the same or have a specified percentage of amino acid residues or nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" J. Mol. Biol. 215:403-410, Gish et al. (1993) "Identification of protein coding regions by database similarity search" Nature Genet. 3:266-272, Madden et al. (1996) "Applications of network BLAST server" Meth. Enzymol. 266:131-141, Altschul et al. (1997) ""Gapped BLAST and PSI-BLAST: a new generation of protein database search programs" Nucleic Acids Res. 25:3389-3402, and Zhang et al. (1997) "PowerBLAST: A new network BLAST application for interactive or automated sequence analysis and annotation" Genome Res. 7:649-656, which are each incorporated by reference. Many other optimal alignment algorithms are also known in the art and are optionally utilized to determine percent sequence identity.

The phrase "in solution" refers to an assay or reaction condition in which the components of the assay or reaction are not attached to a solid support and are present in a liquid medium. Exemplary liquid mediums include aqueous and organic fluids. For example, certain assays of the invention include incubating oligonucleotide probes together with *Candidatus Liberibacter asiaticus* (LAS or HLB) bacteria nucleic acids and LAS nucleic acid amplicons in solution to allow hybridization to occur.

The term "insertion" in the context of a nucleic acid sequence refers to an alteration in which at least one nucleotide is added to the nucleic acid sequence, e.g., at a 5'-terminus, at a 3'-terminus, and/or at an internal position of the nucleic acid sequence.

A "label" refers to a moiety attached (covalently or non-covalently), or capable of being attached, to a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), weakly fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like.

A "linker" refers to a chemical moiety that covalently or non-covalently attaches a compound or substituent group to another moiety, e.g., a nucleic acid, an oligonucleotide probe, a primer nucleic acid, an amplicon, a solid support, or the like. For example, linkers are optionally used to attach oligonucleotide probes to a solid support (e.g., in a linear or other logic probe array). To further illustrate, a linker optionally attaches a label (e.g., a fluorescent dye, a radioisotope, etc.) to an oligonucleotide probe, a primer nucleic acid, or the like. Linkers are typically at least bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Exemplary linkers include, e.g., oligopeptides, oligonucleotides, oligopolyamides, oligoethyleneglycerols, oligoacrylamides, alkyl chains, or the like. Additional description of linker molecules is provided in, e.g., Hermanson, Bioconjugate Techniques, Elsevier Science (1996), Lyttle et al. (1996) Nucleic Acids Res. 24(14):2793, Shchepino et al. (2001) Nucleosides, Nucleotides, & Nucleic Acids 20:369, Doronina et al (2001) Nucleosides, Nucleotides, & Nucleic Acids 20:1007, Trawick et al. (2001) Bioconjugate Chem. 12:900, Olejnik et al. (1998) Methods in Enzymology 291:135, and Pljevaljcic et al. (2003) J. Am. Chem. Soc. 125(12):3486, all of which are incorporated by reference.

A "mixture" refers to a combination of two or more different components. A "reaction mixture" refers a mixture that comprises molecules that can participate in and/or facilitate a given reaction. An "amplification reaction mixture" refers to a solution containing reagents necessary to carry out an amplification reaction, and typically contains primers, a thermostable DNA polymerase, dNTP's, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and, that reaction components are combined prior to the reaction to create a complete reaction mixture. Furthermore, it will be understood by one of skill in the art that reaction components are packaged separately for commercialization and that useful commercial kits may contain any subset of the reaction components, which includes the modified primers of the invention.

A "modified primer nucleic acid" refers to a primer nucleic acid that comprises a moiety or sequence of nucleotides that provides a desired property to the primer nucleic acid. In certain embodiments, for example, modified primer nucleic acids comprise "nucleic acid amplification specificity altering modifications" that, e.g., reduce non-specific nucleic acid amplification (e.g., minimize primer dimer formation or the like), increase the yield of an intended target amplicon, and/or the like. Examples of nucleic acid amplification specificity altering modifications are described in, e.g., U.S. Pat. No. 6,001,611, which is incorporated by reference. Other exemplary primer nucleic acid modifications include a "restriction site linker modification" in which a nucleotide sequence comprising a selected restriction site is attached, e.g., at 5'-terminus of a primer nucleic acid. Restriction site linkers are typically attached to primer nucleic acids to facilitate subsequent amplicon cloning or the like.

A "moiety" or "group" refers to one of the portions into which something, such as a molecule, is divided (e.g., a functional group, substituent group, or the like). For example, an oligonucleotide probe optionally comprises a quencher moiety, a labeling moiety, or the like.

The term "*Candidatus Liberibacter asiaticus,*" "*Candidatus Liberibacter,*" or "*liberobacter*" refers to a genus of gram-native bacteria in the Rhizobiaceae family. Detection of the *liberibacters* can be based on PCR amplification of their 16S rRNA gene with specific primers known in the art or designed for this purpose. Members of the genus are plant pathogens mostly transmitted by psyllids. PCR based methods that have been employed for the detection of *Ca. L. asiaticus bacterium* include multiplex quantitative real-time PCR assays (Saponari et al.) and tissue-blot diagnosis (Nageswara-Rao M. et al), which are each cited in full above and hereby incorporated by reference.

A term "phage" or "bacteriophage" or "bacterial virus" refers to any of a group of viruses that infects and replicates within bacteria. Bacteriophages are composed of proteins that encapsulate a DNA or RNA genome. Their genomes may encode as few as four genes, and as many as hundreds of genes. Phage replicate within bacteria following the injection of their genome into the cytoplasm. Phages are widely distributed in locations populated by bacterial hosts. Phages are seen as a possible therapy against many bacteria. A "virus" is a small infectious agent that replicates only inside the living cells of other organisms. Viruses can infect all types of life forms, from animal and plants to bacteria and archaea.

During infection a phage attaches to a bacterium and inserts its genetic material into the cell. After this a phage follows one of two life cycles, lytic (virulent or viral reproduction) or lysogenic (temperate). Lytic phages take over the machinery of the cell to make phage components. They then destroy, or lyse, the cell, releasing new phage particles. Lysogenic phages incorporate their nucleic acid into the chromosome of the host cell and replicate with it as a unit without destroying the cell. Under certain conditions lysogenic phages can be induced to follow a lytic cycle. A key difference between the lytic and lysogenic phage cycles is that in the lytic phage, the viral DNA exists as a separate molecule within the bacterial cell, and replicates separately from the host bacterial DNA. The location of viral DNA in the lysogenic phage cycle is within the host DNA, therefore in both cases the virus/phage replicates using the host DNA machinery, but in the lytic phage cycle, the phage is a free floating separate molecule to the host DNA.

The term "*Candidatus Liberibacter* nucleic acid" or "*Candidatus Liberibacter asiaticus* nucleic acid" or "bacteria or phage or virus nucleic acid" refers to a nucleic acid (and/or an amplicon thereof) that is derived or isolated from *Candidatus Liberibacter* or *Candidatus Liberibacter asiaticus* or target bacteria, phage, or virus, etc.

The term "nucleic acid" refers to nucleotides (e.g., ribonucleotides, deoxyribonucleotides, dideoxynucleotides, etc.) and polymers that comprise such nucleotides covalently linked together, either in a linear or branched fashion. Exemplary nucleic acids include deoxyribonucleoic acids (DNAs), ribonucleic acids (RNAs), DNA-RNA hybrids, oligonucleotides, polynucleotides, genes, cDNAs, aptamers, antisense nucleic acids, interfering RNAs (RNAis), molecular beacons, nucleic acid probes, peptide nucleic acids (PNAs), locked nucleic acids (LNA™), PNA-DNA conjugates, PNA-RNA conjugates, LNA™-DNA conjugates, LNA™-RNA conjugates, etc.

A nucleic acid is typically single-stranded or double-stranded and will generally contain phosphodiester bonds, although in some cases, as outlined, herein, nucleic acid analogs are included that may have alternate backbones, including, for example and without limitation, phosphoramide (Beaucage et al. (1993) Tetrahedron 49(10):1925 and references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem.

Lett. 805; Letsinger et al. (1988) J. Am. Chem. Soc. 110: 4470; and Pauwels et al. (1986) Chemica Scripta 26: 1419, which are each incorporated by reference), phosphorothioate (Mag et al. (1991) Nucleic Acids Res. 19:1437; and U.S. Pat. No. 5,644,048, which are both incorporated by reference), phosphorodithioate (Briu et al. (1989) J. Am. Chem. Soc. 111:2321, which is incorporated by reference), O-methyl-phosphoroamidite linkages (see Eckstein, Oligonucleotides and Analogues: A Practical Approach, Oxford University Press (1992), which is incorporated by reference), and peptide nucleic acid backbones and linkages (see, Egholm (1992) J. Am. Chem. Soc. 114:1895; Meier et al. (1992) Chem. Int. Ed. Engl. 31:1008; Nielsen (1993) Nature 365: 566; and Carlsson et al. (1996) Nature 380:207, which are each incorporated by reference). Other analog nucleic acids include those with positively charged backbones (Denpcy et al. (1995) Proc. Natl. Acad. Sci. USA 92:6097, which is incorporated by reference); non-ionic backbones (U.S. Pat. Nos. 5,386,023, 5,637,684, 5,602,240, 5,216,141 and 4,469, 863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem: Lett. 4: 395; Jeffs et al. (1994) J. Biomolecular NMR 34:17; and Tetrahedron Lett. 37:743 (1996), which are each incorporated by reference) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) Chem. Soc. Rev. pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic or modified bases, many of which are described, or otherwise referred to, herein. In particular, many non-naturally occurring bases are described further in, e.g., Seela et al. (1991) Hely. Chim. Acta 74:1790, Grein et al. (1994) Bioorg. Med. Chem. Lett. 4:971-976, and Seela et al. (1999) Hely. Chim. Acta 82:1640, which are each incorporated by reference. To further illustrate, certain bases used in nucleotides that act as melting temperature (TO modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

The term "nucleic acid detection reagent" refers to a reagent that detectably binds (e.g., hydrogen bonds in nucleic acid hybridization, in antibody-antigen recognition, or the like, or other types of binding interactions) to a nucleic acid of a desired bacteria, phage, virus, etc. that associated with citrus greening diseases or HLB, a substantially identical variant thereof in which the variant has at least 50%, 60%, 70%, 80%, 90%, 95%, 99% sequence identity to one of said nucleic acids or the variant. A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases, telomerases, polynucleotide phosphorylases, and the like.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al.

(1981) Tetrahedron Lett. 22:1859-1862; the triester method of Matteucci et al. (1981) J. Am. Chem. Soc. 103:3185-3191; automated synthesis methods; or the solid support method of U.S. Pat. No. 4,458,066, or other methods known in the art. All of these references are incorporated by reference.

An oligonucleotide probe is "specific" for a target sequence if the number of mismatches presents between the oligonucleotide and the target sequence is less than the number of mismatches present between the oligonucleotide and non-target sequences that might be present in a sample. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. Thus, the use of target-specific primers under suitably stringent amplification conditions enables the specific amplification of those sequences, which contain the target primer binding sites. Similarly, the use of target-specific probes under suitably stringent hybridization conditions enables the detection of a specific target sequence.

The term "oligonucleotide probe," "probe nucleic acid," or "probe" refers to a labeled or unlabeled oligonucleotide capable of selectively hybridizing to a target nucleic acid under suitable conditions. Typically, a probe is sufficiently complementary to a specific target sequence (e.g., a Candidatus Liberibacter nucleic acid or the variant) contained in a nucleic acid sample to form a stable hybridization duplex with the target sequence under a selected hybridization condition, such as, but not limited to, a stringent hybridization condition. A hybridization assay carried out using the probe under sufficiently stringent hybridization conditions permits the selective detection of a specific target sequence. The term "hybridizing region" refers to that region of a nucleic acid that is exactly or substantially complementary to, and therefore hybridizes to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support or the like. In certain embodiments, an oligonucleotide probe of the invention comprises one or more labels (e.g., a reporter dye, a quencher moiety, etc.), such as a FRET probe, a molecular beacon, or the like, which can also be utilized to detect hybridization between the probe and target nucleic acids in a sample. In some embodiments, the hybridizing region of the oligonucleotide probe is completely complementary to the target sequence. However, in general, complete complementarity is not necessary; stable duplexes may contain mismatched bases or unmatched bases. Modification of the stringent conditions may be necessary to permit a stable hybridization duplex with one or more base pair mismatches or unmatched bases. Sambrook et al., Molecular Cloning: A Laboratory Manual, 3rd Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids.

A "primer nucleic acid" or "primer" is a nucleic acid that can hybridize to a template nucleic acid (e.g., a Candidatus Liberibacter nucleic acid, a substantially identical variant thereof in which the variant has at least 50%, 60%, 70%, 80%, 90%, 95%, 99% sequence identity to one of said nucleic acids or the variant, etc.) and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically comprise hybridizing regions that range from about 8 to about 100 nucleotides in length. Short primer nucleic acids generally utilize cooler temperatures to form sufficiently stable hybrid complexes with a template nucleic acid. A primer nucleic acid that is at least partially complementary to a subsequence of a template nucleic acid is typically sufficient to hybridize with the template for extension to occur.

A primer nucleic acid can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art. One of skill in the art will recognize that, in certain embodiments, primer nucleic acids can also be used as probe nucleic acids.

A "subsequence" or "segment" refers to any portion of an entire nucleic acid sequence. A "substantially identical variant" in the context of nucleic acids or polypeptides, refers to two or more sequences that have at least 85%, typically at least 90%, more typically at least 95% nucleotide or sequence identity to one another when compared and aligned for maximum correspondence, as measured using, e.g., a sequence comparison algorithm or by visual inspection. The substantial identity generally exists over a region of the sequences that is at least about 15 nucleotides or amino acids in length, more typically over a region that is at least about 20 nucleotides or amino acids in length, and even more typically the sequences are substantially identical over a region of at least about 25 nucleotides or amino acids in length. In some embodiments, for example, the sequences are substantially identical over the entire length of the nucleic acids or polypeptides being compared. The term "substitution" in the context of a nucleic acid sequence refers to an alteration in which at least one nucleotide of the nucleic acid sequence is replaced by a different nucleotide. The terms "target sequence," "target region," and "target nucleic acid" refer to a region of a nucleic acid, which is to be amplified, detected, or otherwise analyzed.

A "terminator nucleotide" refers to a nucleotide, which upon incorporation into a nucleic acid prevents further extension of the nucleic acid, e.g., by at least one nucleotide incorporating biocatalyst.

A "thermostable enzyme" refers to an enzyme that is stable to heat, is heat resistant and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. Nos. 4,683,202 and 4,683,195, which are both incorporated by reference. As used herein, a thermostable polymerase is typically suitable for use in a temperature cycling reaction such as the polymerase chain reaction ("PCR"). For a thermostable polymerase, enzymatic activity refers to the catalysis of the combination of the nucleotides in the proper manner to form primer extension products that are complementary to a template nucleic acid (e.g., selected subsequences of *Candidatus Liberibacter* (LAS) genome).

A "quencher moiety" or "quencher" refers to a moiety that reduces and/or is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Exemplary quenchers are provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

The term "sample" refers to any substance containing or presumed to contain one or more host and/or pathogen nucleic acids including, but not limited to, tissue or fluid isolated from one or more subjects or individuals, in vitro cell culture constituents, as well as clinical samples. Exemplary samples include bacteria, virus, plant, animal or mammal sample including blood, plasma, serum, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like.

The phrase "sample derived from a subject" refers to a sample obtained from the subject, whether or not that sample undergoes one or more processing steps (e.g., cell lysis, debris removal, stabilization, etc.) prior to analysis. To illustrate, samples can be derived from subjects by scraping, venipuncture, swabbing, biopsy, or other techniques known in the art.

A "sequencing reaction" refers to a reaction that includes, e.g., the use of terminator nucleotides and which is designed to elucidate the sequence of nucleotides in a given nucleic acid. A "set" refers to a collection of at least two things. For example, a set may include 2, 3, 4, 5, 10, 20, 50, 100, 1,000 or other number of molecule or sequence types. For example, certain aspects of the invention include reaction mixtures having sets of amplicons. A "subset" refers to any portion of a set.

A "solid support" refers to a solid material that can be derivatized with, or otherwise attached to, a chemical moiety, such as an oligonucleotide probe or the like. Exemplary solid supports include plates, beads, microbeads, tubes, fibers, whiskers, combs, hybridization chips (including microarray substrates, such as those used in GeneChip™ probe arrays (Affymetrix, Inc., Santa Clara, Calif., USA) and the like), membranes, single crystals, ceramic layers, self-assembling monolayers, and the like.

A "subject" refers to an organism. Typically, the organism could be a bacteria organism, viral organism, plant organism, animal or a mammalian organism including a human organism. In certain embodiments, for example, a subject is a plant or tree suspected of having LAS or citrus greening infection or disease, such as HLB.

The invention provides a novel pathogenesis model illustrating archaic phage infection of HLB. More specifically, the invention provides that under stress and/or in the presence of inducers or modulators of plant or bacterial origin, the phage genes attach/adsorb to the bacterial targeted genes result in peptidoglycan destruction in preparation of "burst", as well as phage protein production and phage assembly ("Burst Marker") followed by phage release in the lytic stage where the bacterial components, such as phage particles, bacterial cell wall, starch, remnant peptidoglycan and cellular contents, are released simultaneously in Lytic Phage Burst (LPB), resulting in "greening effect" where downstream phloem and/or leaves are clogged and dried up in a "river bed" corky appearance, and transpiration is halted for this section of tree independent of other systemic nutrient routes (see FIGS. 1, 3, 4, and 5).

FIG. 1 illustrates a novel pathogenesis model. This model illustrates that under stress (103), e.g., in the presence of inducers or modulators of plant or bacterial origin (104), the phage genes (101) attach/adsorb to the bacterial targeted genes (102) result in phage protein production and phage assembly ("Burst Marker") (106) and peptidoglycan (105) destruction in preparation of "burst" followed by phage release in the "lytic stage" (107) where the bacterial components are released. In certain embodiments, the released bacterial starch glucose molecules (108) clog phloem of stems & leaves (109), in a manner similar to human heart disease, thus, blocking normal transpiration.

Figure 2:
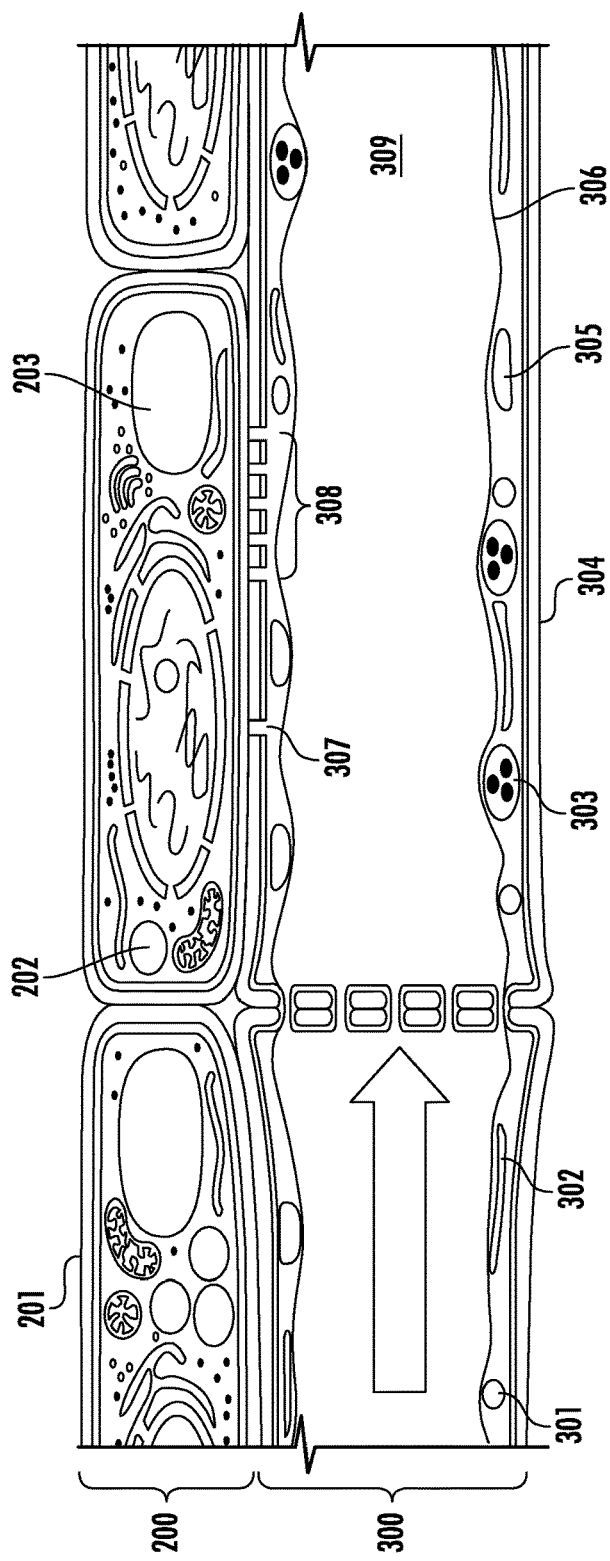
FIG. 2 illustrates normal pores in angiosperm sieve tube elements and companion cells.

FIG. 2 illustrates normal pores in angiosperm sieve tube elements and companion cells. The cell wall (201), plastid (202), and vacuole (203) of the companion cell (200), and the mitochondrion (301), degenerating SER (302), plastid (303), cell wall (304), P-protein (305), degenerate tonoplast (306), as well as large plasmodesmate (307), sieve area (308), and lumen (309) of the sieve element (300) are illustrated in the figure. The figure also illustrates normal transpiration flow in the direction of the arrow through these normal pores.

Figure 3:
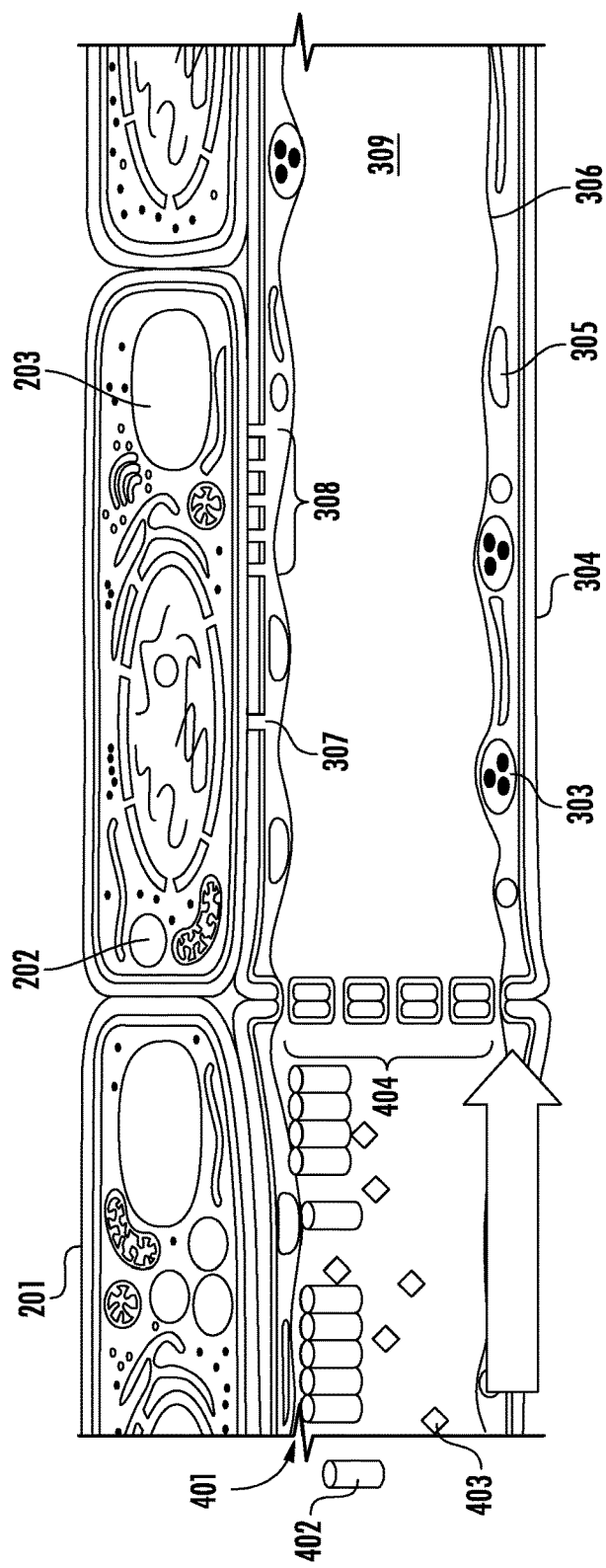
FIG. 3 illustrates HLB flagellated in angiosperm sieve tube elements and companion cells.
Figure 4:
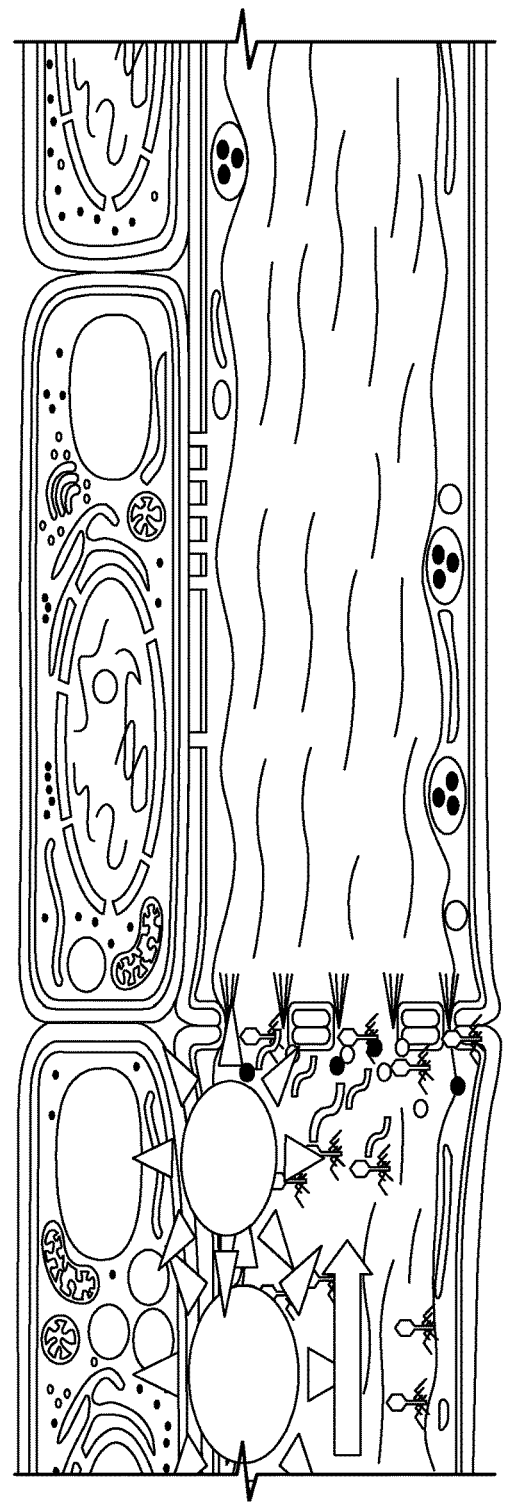
FIG. 4 illustrates blocked pores where phage particles, bacterial cell wall, starch, remnant peptidoglycan and cellular contents are released simultaneously in Lytic Phage Burst (LPB).
Figure 5:
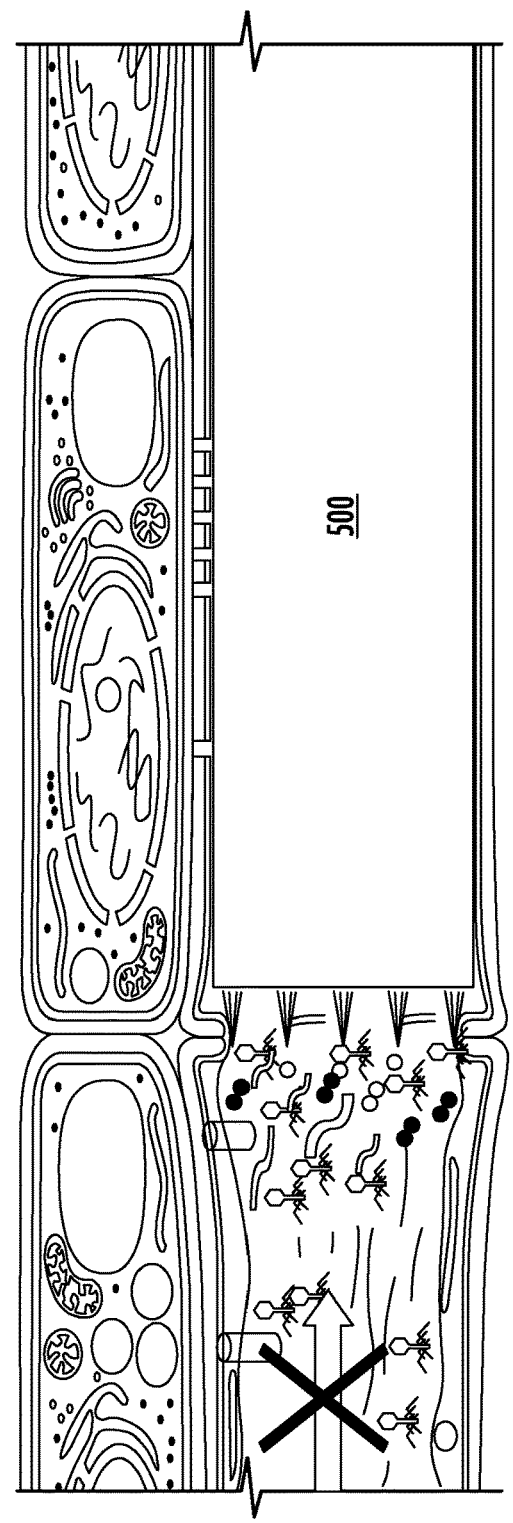
FIG. 5 illustrates the "Greening Effect" where downstream phloem is dried up in a "river bed" corky appearance. Transpiration is halted for this section of tree independent of other systemic nutrient routes.

FIG. 3 illustrates HLB flagellated in angiosperm sieve tube elements and companion cells wherein biofilm (401) is formed when bacteria are under stress (inducer) (403) resulting in HLB (402), forming sieve plate (404), thus, leading to blocking the normal transpiration, as shown in FIGS. 4 and 5.

FIG. 4 illustrates blocked pores of the sieve plate where phage particles, bacterial cell wall, starch, remnant peptidoglycan and/or cellular contents are released simultaneously in Lytic Phage Burst (LPB).

FIG. 5 illustrates the "Greening Effect" where downstream phloem (500) is dried up in a "river bed" corky appearance. Transpiration is halted for this section of tree independent of other systemic nutrient routes.

Certain embodiments of the invention provide phage production in HLB. Functional holin activity of the SC1_gp110 gene confirms the annotation. In certain embodiments, the invention provides that expression analyses revealed much higher levels of expression of phage late genes, particularly the holin, in periwinkle as compared to citrus, indicating a phage response specific to periwinkle. In other embodiments, the significant increase in holin mRNA levels in citrus, 12 to 24 hours after being detached, regardless of temperature, indicates a potential lysis triggering signal in citrus. In yet other embodiments, the holin promoter region was developed into a reporter gene construct that is useful for monitoring lytic activation by potential inducers in citrus, and it was demonstrated that the mode of action of thermal therapy (heat curing of Las) in infected citrus does not seem to be connected to phage induction.

The invention further provides a selective detection of one or more pathogens in a subject based on molecular biology techniques and reagents. In particular, based on new detection strategies utilizing quantitative load test with at least two (2) or three (3) targets from at least two different organisms that are pathogenically tied together to derive a pathogenic ratio or load or index used in diagnosis, prognosis and/or treatment of any disease involving virus or phage in a ratio to host (e.g., bacteria or plant) in plants and/or animals or mammals including humans. More specifically, based on the methods and reagents described herein, *Candidatus Liberibacter asiaticus* (LAS) or citrus greening infections can be diagnosed by utilizing a phage DNA or RNA quantification as a pathogenic ratio of pathogenesis with its host, i.e., the LAS bacteria genome, for reporting pathogenesis and treatment strategy with clinical utility. In addition to detection methods and reaction mixtures, the invention also provides kits and systems for detecting these pathogenic agents, as well as the use of the systems or an in vitro cell culture model comprising a phage lytic cycle repressor for drug screening for treating and preventing HLB and citrus greening. Moreover, the invention provides methods and compositions of treatment and prevention of HLB and citrus greening using any antiviral agents including, but not limited to, nucleoside, nucleotide, ribonucleoside or analogs thereof, with or without a nucleotide pool reducer, such as hydroxyurea. Furthermore, the invention provides that the treatment or prevention composition can further comprise a surfactant or penetrant to facilitate drug delivery to the target location of the subject for better targeted treatment.

Pathogen Load or Pathogen Index for Diagnostic and Prognosis of Pathogenesis and/or Citrus Greening Blight, such HLB or LAS The invention provides a novel pathogenesis model for diagnostic, prognostic, and treatment methods in a biological sample.

In certain embodiments, the invention provides a method for detecting pathogenesis in a biological sample, comprising: a) quantifying the amount of a nucleic acid in the sample specific for a first organism that is a pathogen associated with a second organism that in tandem these two organisms affects a host organism to determine a pathogen quantitative measurement, b) quantifying the amount of a nucleic acid in the sample specific for the host organism response to pathogens to determine a multiplex quantitation for targets associated with the pathogenesis of the disease; and c) calculating the ratio of the amount of dual pathogen targets relative to the amount of host quantitative measures, wherein said ratio provides a pathogenic index for detecting pathogenesis. In certain embodiments, a greater pathogenic index indicates a poorer prognosis and can be used for drug treatment efficacy and drug screening.

In certain embodiments, the quantification of the nucleic acid in the sample specific for the first organism is performed by contacting the nucleic acid from the sample with a first set of oligonucleotide primers in a nucleic acid amplification reaction, the first set of oligonucleotides being at least partially complementary to the nucleic acid of the first organism, and wherein the quantification of the nucleic acid in the sample specific for the second organism is performed by contacting the nucleic acid from the sample with a second set of oligonucleotide primers in a nucleic acid amplification reaction, the second set of oligonucleotides being at least partially complementary to the nucleic acid of the second organism, and further comprising detecting amplicons from the nucleic acid amplification reactions, and wherein the quantification of the nucleic acid in the sample specific for the third host organism is performed by contacting the nucleic acid from the sample with a third set of oligonucleotide primers in a nucleic acid amplification reaction, the third set of oligonucleotides being at least partially complementary to the nucleic acid of the third organism, and further comprising detecting amplicons from the nucleic acid amplification reactions, wherein the amplification reactions can occur in the same container, and calculating the ratio of the amount of pathogen ratio relative to the amount of host load based on the relative number of amplicons to derive the pathogenic index or quartile. As used herein, the pathogen organism is a virus or bacteria, and the host organism is a bacteria, plant or animal. When the host organism is a bacteria, the host may also reside within or in association with another host, such as a plant or animal, e.g., human. In certain embodiments, the pathogenesis is citrus green blighting or Huanglongbin (HLB), the pathogen or the first organism can be a bacterio-phage or virus, and the second organism is *Candidatus Liberibacter asiaticus* (LAS) bacteria and the host is a wide array of fruiting and non-fruiting plants. The pathogenic index may also be derived from a further correlation with any inducer or factor gene pathogenically tied together with the dual pathogen to host relationship. In certain embodiments, the second organism is a lytic bacteriophage, including but not limited to, SC1, SC2, and SC3 lytic phage.

The nucleic acid quantified in the invention method includes, but is not limited to, RNA or DNA. In certain embodiments, the phage RNA and the bacterial DNA are quantified, and a ratio of phage RNA to bacterial DNA is calculated to derive a pathogen index or quartile. The nucleic acid can be amplified by any conventional nucleic acid amplification reactions for quantitation (e.g., qPCR) including, but not limited to standard polymerase chain reaction (PCR), real-time PCR (e.g., Roche, HIV-1 Cobas Taqman system; Abbot HIV-1 M2000 System), recombinase polymerase amplification (RPA), helicase-dependent amplification (HAD), loop mediate isothermal amplification (LAMP), and nicking enzyme amplification reaction (NEAR). Details describing qPCR and/or real-time PCR can be found in U.S. Pat. Nos. 5,972,716; 6,800,452; 6,746,864; 7,427,380; 7,238,321; and 8,058,054, and Tatineni et al. (2008, Phytopathology 98(5):592-99), the entire contents of each of which are incorporated by reference herein. Furthermore, the detailed descriptions of the RPA amplification are provided for instance in U.S. Pat. Nos. 7,485,428; 7,666,598; 7,763,427; and 7,759,061, the entire contents of each of which are incorporated by reference herein; the detailed descriptions of the HAD amplification are provided for instance in U.S. Pat. Nos. 7,829,284; 7,282,328; and 7,662,594, the entire contents of each of which are incorporated by reference herein; and the detailed descriptions of the LAMP amplification are provided for instance in U.S. Pat. Nos. 7,851,186; 7,745,135; and 6,974,670, the entire contents of each of which are incorporated by reference herein.

In certain embodiments, the invention provides a kit for detecting citrus greening blight in a sample, comprising: a) a first set of oligonucleotides being at least partially complementary to a nucleic acid of a first pathogen organism in the sample that is pathogenically associated with citrus greening blight, b) a second set of oligonucleotides being at least partially complementary to a nucleic acid of a second organism that is a host to the pathogen organism in the same sample, c) reagents for nucleic acid amplification reactions with the first and second sets of oligonucleotides; d) instructions for conducting the nucleic acid amplification reactions and detecting one or more amplicons thereof; and e) instructions for calculating a ratio of the amplicons wherein said ratio provides a pathogenic index for detecting, prognosis, and treatment for citrus greening blight.

Typically, at least one of the nucleic acid detection reagents comprises at least one label and/or at least one quencher moiety. To illustrate, the label optionally comprises a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like.

The nucleic acid detection reagents of the invention are provided in various formats. In some embodiments, for example, at least one of the nucleic acid detection reagents is in solution. In other embodiments, a solid support comprises at least one of the nucleic acid detection reagents. In these embodiments, the nucleic acid detection reagents are non-covalently or covalently attached to the solid support. Exemplary solid supports utilized in these embodiments are optionally selected from, e.g., a plate, a microwell plate, a bead, a microbead (e.g., a magnetic microbead, etc), a tube (e.g., a microtube, etc.), a fiber, a whisker, a comb, a hybridization chip, a membrane, a single crystal, a ceramic layer, a self-assembling monolayer, and the like.

To further illustrate, the nucleic acid detection reagents are optionally conjugated with biotin or a biotin derivative and the solid support is optionally conjugated with avidin or an avidin derivative, or streptavidin or a streptavidin derivative. In some embodiments, a linker attaches the nucleic acid detection reagents to the solid support. The linker is typically selected from, e.g., an oligopeptide, an oligonucleotide, an oligopolyamide, an oligoethyleneglycerol, an oligoacrylamide, an alkyl chain, and the like. Optionally, a cleavable attachment attaches the nucleic acid detection reagents to the solid support. The cleavable attachment is generally cleavable by, e.g., heat, an enzyme, a chemical agent, electromagnetic radiation, etc.

The kit also includes one or more of: a set of instructions for contacting the nucleic acid detection reagents with nucleic acids from a sample or amplicons thereof and detecting binding between the nucleic acid detection reagents and the target nucleic acids, if any, or at least one container for packaging the nucleic acid detection reagents and the set of instructions. Exemplary solid supports include in the kits of the invention are optionally selected from, e.g., a plate, a microwell plate, a bead, a microbead, a tube (e.g., a microtube, etc.), a fiber, a whisker, a comb, a hybridization chip, a membrane, a single crystal, a ceramic layer, a self-assembling monolayer, or the like.

Diagnostic, Prognostic, and Treatment Report:

The invention further provides a report comprising a report algorithm correlated with the pathogenic index providing clinical utility as a treatment strategy. The TRUGENE® HIV-1 Genotyping Kit (Visible Genetics, Siemens) is exemplary of a report algorithm with clinical utility used as a treatment strategy. In particular, the TRUGENE HIV-1 Genotyping Assay is based upon several processes culminating in a data analysis step, wherein gene sequences are analyzed by a software system to provide a TRUGENE HIV-1 Resistance Report that is useful for the therapeutic management of HIV in a patient, also see U.S. Pat. Nos. 6,830,887; 6,653,107; 6,265,152; 6,007,983; 5,795,722; 5,834,189; and 5,545,527, the entire contents of each of which are incorporated by reference herein.

In some embodiments, the invention method comprises a step of quantifying the amount of a nucleic acid in the sample specific for host bacteria, phage pathogen, and an inducer of the pathogen organism to determine a host load, a pathogen load, and an inducer load; and wherein the pathogenic index, host or pathogen load, and/or the inducer load are correlated with the report index for determining prognosis and providing clinical utility as a treatment strategy. The invention method further provides that multiple unique nucleic acids specific to the pathogen organism, the host organism or the inducer are quantified and correlated in the report index.

Cultivation of Citrus Greening Blight for Screening a Treatment Therapeutic or Research The invention further provides a method for screening a candidate therapeutic agent for inhibition or prevention of citrus greening blight. Cultivation of '*Candidatus Liberibacter asiaticus*', '*Ca. L. africanus*' and '*Ca. L. americanus*' associated with Huanglongbing is reported in Sechler et al. (2009, Phytopathology 99 (5):480-86), the entire content of which is incorporated by reference herein. The invention method comprises the steps of providing a culture of *Candidatus Liberibacter* with a bacteriophage having a repressed phage lytic cycle; combining the culture with a candidate therapeutic agent candidate; and detecting inhibition of growth of the *Candidatus Liberibacter* culture indicating that the candidate therapeutic agent inhibits or prevents citrus greening blight. In certain embodiments, the bacteriophage is a lytic phage, including but not limited to, SC1, SC2, and SC3 lytic phage, and wherein the phage lytic cycle is repressed or genetically deleted. In some embodiment, the citrus greening blight bacteria, such as the HLB bacteria *Candidatus Liberibacter* is cultured in a culture media containing a repressor to phage lytic cycle of a bacteriophage. The invention encompasses any cell culture media and system suitable for growing any bacteria cultures. The invention also encompasses any phage lytic cycle repressor or inhibitor, now known or later developed in the art, including but not limited to SC1 repressors SC1_gp110 (holin), SC1_gp025, SC1_gp-95, SC2_gp100, C1 or phage lambda repressor (e.g., phage 434, P22), see Exploiting the Las and Lam phage for potential control of HLB, Citrus Advanced Technology Program, final report submitted on Aug. 7, 2013 by Citrus Research and Development Foundation, the entire report is incorporated by reference herein.

Prevention and Treatment of Bacteriophage or Viral Infection

The invention also provides a method for treating and/or preventing bacteriophage or viral infection in bacteria, plant or animal individual, said method comprising administering to the individual in need a composition comprising an effective amount of an agent selected from the group consisting of nucleoside, non-nucleoside, nucleotide, non-nucleotide, ribonucleoside, and a ribonucleoside analog that selectively inhibits viral replication. Nucleosides can be phosphorylated by specific kinases in the cell on the sugar's primary alcohol group ($-CH_2-OH$), producing nucleotides, which are the molecular building-blocks of DNA and RNA. Nucleosides can be produced by de novo synthesis pathways, in particular in the liver, but they are more abundantly supplied via ingestion and digestion of nucleic acids in the diet, whereby nucleotidases break down nucleotides (such as the thymidine monophosphate) into nucleosides (such as thymidine) and phosphate. The nucleosides, in turn, are subsequently broken down in the lumen of the digestive system by nucleosidases into nucleobases and ribose or deoxyribose. In addition, nucleotides can be broken down inside the cell into nitrogenous bases, and ribose-1-phosphate or deoxyribose-1-phosphate.

Several nucleoside analogues are also used as antiviral or anticancer agents. Nucleoside analogues are molecules that act like nucleosides in DNA synthesis. They include a range of antiviral products used to prevent viral replication in infected cells. The most commonly used is acyclovir (ACV). The use of nucleoside, non-nucleoside, nucleotide, non-nucleotide, ribonucleoside, a ribonucleoside analog, and a nucleotide pool reducer are known in the art for treatment of viral infection, such as for example, the treatment of human immunodeficiency viruses. The viral polymerase incorporates these compounds with non-canonical bases. These compounds are activated in the cells by being converted into nucleotides. They are administered as nucleosides since charged nucleotides cannot easily cross cell membranes.

Exemplary nucleoside analogue drugs include, but not limited to deoxyadenosine analogues (e.g., DIDANOSINE (ddI)(HIV) and VIDARABINE (chemotherapy)), deoxycytidine analogues (e.g., CYTARABINE (chemotherapy), EMTRICITABINE (FTC)(HIV), LAMIVUDINE (3TC) (HIV, hepatitis B), and ZALCITABINE (ddC)(HIV)), deoxyguanosine analogues (e.g., ABACAVIR (HIV) and Entecavir (hepatitis B)), (deoxy-)thymidine analogues (e.g., STAVUDINE (d4T), TELBIVUDINE (hepatitis B), ZIDOVUDINE (azidothymidine, or AZT)(HIV)), and deoxyuridine analogues (e.g., Idoxuridine and Trifluridine).

The invention encompasses any nucleoside or nucleoside analogs, now known or later developed in the art that are capable of treating a viral infection. Exemplary nucleoside antiretroviral agents include, but not limited to, ZIDOVUDINE® (ZDV, AZT), EPIVIR® (3TC, lamivudine), EMTRIVA® (FTC, emtricitabine), VIREAD® (tenofovir disoproxil fumarate, TDF), ZIAGEN® (abacavir sulfate, ABC), CARBOVIR® (CBV), Racivir [RCV, (±)-β-2',3'-dideoxy-5-fluoro-3'-thiacytidine], DEXELVUCITABINE® (β-D-2',3'-didehydro-2',3'-dideoxy-5-fluorocytidine, reverset, RVT, D-D4FC, DFC), AMDOXOVIR® [AMDX, (−)-β-D-2,6-diaminopurine dioxolane, DAPD], 9-(beta-D-1,3-Dioxolan-4-yl)guanine (DXG), AVX754 [SPD-754, (−)dOTC, (−)-2'-deoxy-3'-oxa-4'-thiocytidine]. Non-nucleoside reverse transcriptase inhibitors (NNRTIs) represent another class of drugs that may be used in the present invention, and may be selected from NNRTIs such as are used for treating HIV infections, such as efavirenz (SUSTIVA®), rilpivirine (EDURANT®), etravirine (INTELENCE®), delavirdine (RESCRIPTOR®), nivirapine (VIRAMUNE®) and lersivirine. See also U.S. Pat. Nos. 8,415,321; 8,168,583; 7,635,690; 7,402,588; 7,115,584; 6,949,521; and 5,990,093, the entire contents of each of which are incorporated by reference herein.

The amount of a nucleoside or analog thereof that may be used alone or in combination with a pharmaceutically acceptable carrier to produce a single dosage form will vary depending upon the host treated and the particular mode of administration. It will be appreciated by those skilled in the art that the unit content of a nucleoside or analog thereof contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

The dosage regime for treating or preventing bacteriophage or viral infection in bacteria, plant or animal individual with a nucleoside or analog thereof of the invention is selected in accordance with a variety of factors, including the type, age, weight, sex, diet and medical condition of the subject, the route of administration, pharmacological considerations such as activity, efficacy, pharmacokinetic and toxicology profiles of the particular compound employed, whether a nucleoside delivery system is utilized and whether the nucleoside is administered as a pro-drug or part of a drug combination. Thus, the dosage regime actually employed may vary widely from subject to subject.

Any antiviral agent including the nucleoside or analog thereof used in the present invention can be synthesized chemically and/or produced by any suitable mythology and/or technology known to those skilled in the art, and can be formulated by known methods for administration to a subject using several suitable routes including but not limited to, systemic or local administration depending on the subject being treated or administered. The individual antiviral agent may also be administered in combination with one or more other antiviral agent and/or together with other biologically active or biologically inert agents. Such biologically active or inert agents may be in fluid or mechanical communication with the antiviral agent or attached to the antiviral by ionic, covalent, Van der Waals, hydrophobic, hydrophillic or other physical forces.

The antiviral agent, such as nucleoside or analog thereof, of the present invention may be formulated by any conventional manner using one or more pharmaceutically acceptable carriers and/or excipients. The antiviral agent of the invention may take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins PA, USA (2000).

The nucleoside or analog thereof may also take the form of solutions, suspensions, emulsions, tablets, pills, capsules, powders, controlled- or sustained-release formulations and the like. Such formulations will contain an effective amount of the nucleoside or analog thereof preferably in purified form, together with a suitable amount of carrier so as to provide the form for proper administration to the patient. The formulation should suit the mode of administration.

An effective amount of an antiviral agent (e.g., nucleoside or analog thereof) relates generally to the amount needed to achieve a preventive or therapeutic objective, administration rate, and depletion or metabolic rate of the antiviral agent from a subject. Common ranges for effective doses, as well as dosing frequencies may vary depending on the factors discussed above.

In some embodiments, the treatment and/or prevention method may also include a nucleotide pool reducer. In one aspect the nucleotide pool reducer is hydroxyurea or hydroxycarbamide. While not intending to be bound by theory, hydroxyurea has been shown to inhibit the de novo synthesis of deoxyribonucleotides, deplete deoxyribonucleoside triphosphate pools and starve host cell and viral replication of precursor molecules, such as described in Hendricks and Matthews, 1998, and which is incorporated by reference herein.

In another aspect, the method for treating citrus greening blight includes administering a composition comprising a surfactant or penetrant for enhancing delivery of the composition. The term surfactant or penetrant means one or more compounds that improve and/or accelerate the delivery of the composition. In certain embodiments, the invention composition comprises a penetrant under a trade name Atomic Grow, manufactured by NanoCanopy. The invention encompasses any other surfactant or penetrant, now known or later developed in the art, for the same purposes. Various administration strategies for delivery to plants are well-known in the art.

Each of the publications referred to herein is hereby incorporated by reference in its entirety, for all purposes.

This invention has been described with reference to its preferred embodiments. Variations and modifications of the invention, will be obvious to those skilled in the art from the foregoing detailed description of the invention.

The invention claimed is:

1. A method for detecting pathogenesis in a biological sample, comprising:
   a) quantifying an amount of a nucleic acid in the biological sample specific for a first organism that is a pathogen associated with a second organism, wherein in tandem the first and second organisms affect pathogenesis of a host organism, to determine a pathogen quantitative measurement,
   b) quantifying an amount of a nucleic acid in the biological sample specific for the second organism, to determine a second organism quantitative measurement;
   c) quantifying an amount of a nucleic acid in the sample specific for the host organism response to the pathogen, to determine a multiplex quantitation for targets associated with the pathogen of a disease; and
   d) calculating a ratio of the amount of dual pathogen targets relative to the amount of host quantitative measures, wherein said ratio provides a pathogen index for detecting pathogenesis.

2. The method of claim 1, wherein said pathogen index indicates a prognosis of the pathogenesis or can be used for drug treatment efficacy and drug screening.

3. The method of claim 1, wherein the quantification of the nucleic acid in the sample specific for the first organism is performed by contacting the nucleic acid from the sample with a first set of oligonucleotide primers in a nucleic acid amplification reaction, the first set of oligonucleotides being at least partially complementary to the nucleic acid of the first organism, and wherein the quantification of the nucleic acid in the sample specific for the second organism is performed by contacting the nucleic acid from the sample with a second set of oligonucleotide primers in a nucleic acid amplification reaction, the second set of oligonucleotides being at least partially complementary to the nucleic acid of the second organism, and wherein the quantification of the nucleic acid in the sample specific for the host organism is performed by contacting the nucleic acid from the sample with a third set of oligonucleotide primers in a nucleic acid amplification reaction, the third set of oligonucleotides being at least partially complementary to the nucleic acid of a third organism, and further comprising detecting amplicons from the nucleic acid amplification reactions, further comprising
   detecting amplicons from the nucleic acid amplification reactions, wherein the amplification reactions occur in the same container, and
   calculating the ratio of the amount of pathogen ratio relative to the amount of host load based on the relative number of amplicons to derive a pathogenic index or quartile.

4. The method of claim 1, wherein said pathogen first organism is a virus or bacteria.

5. The method of claim 1, wherein said host organism is a bacteria, plant or animal.

6. The method of claim 1, wherein said host is a citrus plant and said pathogenesis is citrus green blighting or Huanglongbin (HLB).

7. The method of claim 6, wherein said second organism is *Candidatus Liberibacter asiaticus* (LAS).

8. The method of claim 1, further comprising correlating a report algorithm or index with a pathogenic index or quartile providing clinical utility as a treatment strategy or for drug screening.

9. The method of claim 8, further comprising a step of quantifying the amount of a nucleic acid in the sample specific for an inducer of the pathogen organism to determine an inducer load; and wherein the pathogen index and the inducer load are correlated with the report index for determining prognosis and providing clinical utility as a treatment strategy or drug screening.

10. The method of claim 9, wherein multiple unique nucleic acids specific to the pathogen organisms, the host organism or the inducer are quantified and correlated in the report index.

* * * * *